(12) United States Patent
Schuster et al.

(10) Patent No.: US 9,976,292 B1
(45) Date of Patent: May 22, 2018

(54) FLUSH ACTIVATED AIR FRESHENER

(75) Inventors: Michael J. Schuster, Joliet, IL (US);
Douglas C. Saunders, Plainfield, IL (US); Duston E. A. Stutzman, Plainfield, IL (US)

(73) Assignee: Danco, Inc., Irving, TX (US)

( * ) Notice: Subject to any disclaimer, the term of this patent is extended or adjusted under 35 U.S.C. 154(b) by 1918 days.

(21) Appl. No.: 13/293,486

(22) Filed: Nov. 10, 2011

Related U.S. Application Data (60) Provisional application No. 61/412,658, filed on Nov. 11, 2010.

(51) Int. Cl.
*E03D 9/00* (2006.01)

(52) U.S. Cl.
CPC .................................. *E03D 9/007* (2013.01)

(58) Field of Classification Search
CPC ............... E03D 9/007; A61L 9/05; A61L 9/12
USPC ........................................................ 4/228.1
See application file for complete search history.

(56) References Cited

U.S. PATENT DOCUMENTS

| | | | | |
|---|---|---|---|---|
| 4,064,573 A | * | 12/1977 | Calderone | 4/228.1 |
| 4,625,342 A | * | 12/1986 | Gangnath et al. | 4/228.1 |
| 5,675,845 A | * | 10/1997 | Martin et al. | 4/228.1 |
| 6,785,911 B1 | * | 9/2004 | Percher | 4/228.1 |
| 2002/0069457 A1 | * | 6/2002 | Meier et al. | 4/226.1 |
| 2002/0166871 A1 | * | 11/2002 | Muderlak et al. | 222/23 |
| 2003/0188377 A1 | * | 10/2003 | Contadini et al. | 4/222 |
| 2007/0204388 A1 | * | 9/2007 | Zyskowski et al. | 4/228.1 |
| 2011/0004986 A1 | * | 1/2011 | Vu | 4/223 |

* cited by examiner

*Primary Examiner* — Janie Loeppke (74) *Attorney, Agent, or Firm* — Thomas |Horstemeyer, LLP (57) ABSTRACT

Various systems and methods are provided for flush activated air freshening. In one embodiment, a method includes sensing the initiation of a flush of a toilet system and discharging aerosol in response to sensing the initiation of the flush. In another embodiment, an air freshener assembly for a toilet system includes a control valve coupled to an aerosol cartridge and a spray control configured to activate the control valve to discharge aerosol from the aerosol cartridge in response to initiation of a flush of the toilet system. In another embodiment, a toilet system includes means for initiating a flush of a toilet, means for sensing initiation of the flush, and means for discharging aerosol in response to sensing the initiation of the flush.

22 Claims, 14 Drawing Sheets

FLUSH ACTIVATED AIR FRESHENER

CROSS REFERENCE TO RELATED APPLICATIONS

This application claims priority to copending U.S. provisional application entitled "FLUSH ACTIVATED AIR FRESHENER" having serial no. 61/412,658, filed Nov. 11, 2010, the entirety of which is hereby incorporated by reference.

BACKGROUND

Unpleasant odors may be neutralized by masking with a pleasing fragrance, eliminating with a disinfectant, or a combination of the two. Candles, incense, reed diffusers, and hand operated aerosol spray cans have been used to counter the offensive odors when they occur.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the disclosure. Moreover, in the drawings, like reference numerals designate corresponding parts throughout the several views.

DETAILED DESCRIPTION

Disclosed herein are various embodiments of systems and methods related to flush activated air fresheners. Reference will now be made in detail to the description of the embodiments as illustrated in the drawings, wherein like reference numbers indicate like parts throughout the several views.

Figure 1:
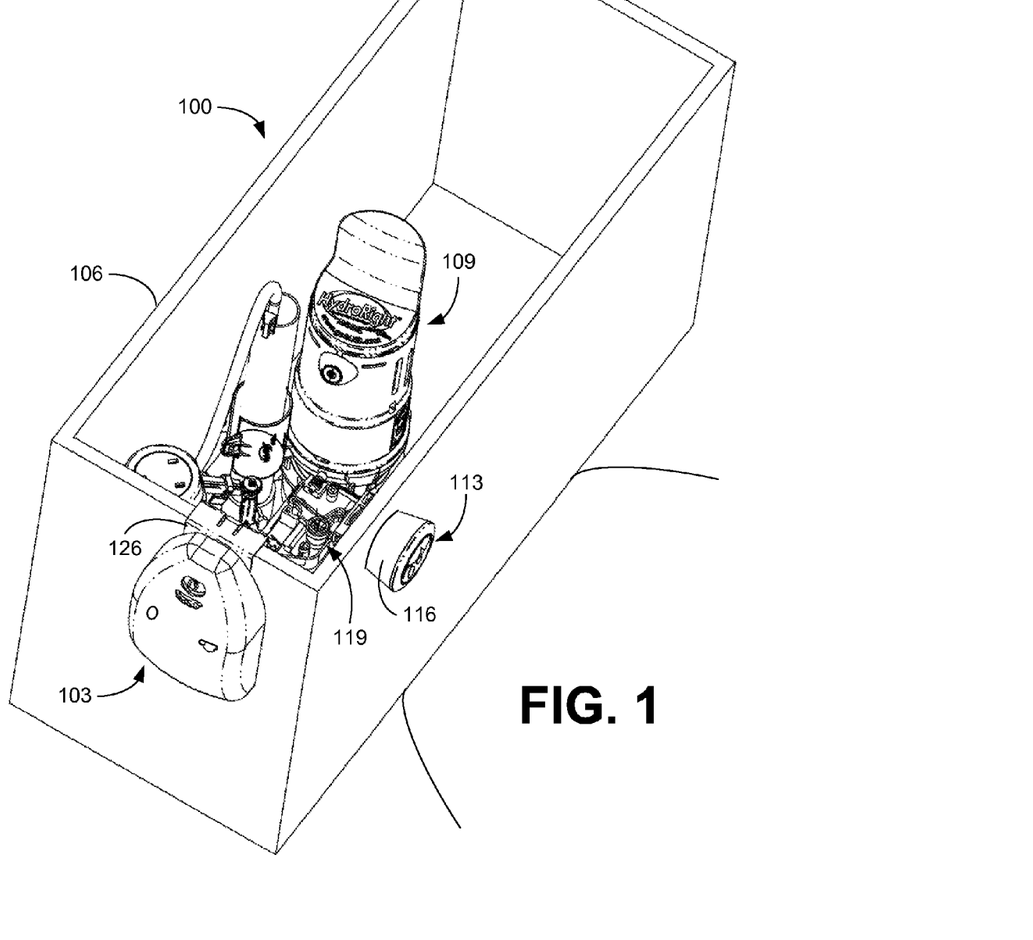
FIG. 1 is a drawing of a toilet including an air freshener assembly according to various embodiments of the disclosure.

It is not uncommon for offensive odors to be present in bathrooms, restrooms, or other facilities with toilets. Air fresheners and deodorizers are commonly applied using an aerosol spray can that is manually operated by a user pressing an actuator valve or cap. The application of the aerosol sprays may be tied to operation of the toilet. Referring to FIG. 1, shown is an example of a toilet 100 including an air freshener assembly 103 that is activated by flushing the toilet 100. The air freshener assembly 103 may affixed to a wall of the tank 106 of the toilet 100 by a mounting clip 126 or other appropriate fastener. In other embodiments, the air freshener assembly 103 may be positioned in other locations such as, but not limited to, on a wall, on a counter, or at another location on the toilet 100.

The toilet 100 also includes an activation assembly 113 in communication with a flush assembly 109 such as, but not limited to, a dual flush assembly. In the embodiment of FIG. 1, the activation assembly 113 includes a push button assembly 116 that is detachably connected to an actuation control box 119 (shown as a cut away view). The push button assembly 116 includes one or more button(s) that, when depressed, initiate appropriate operation of the flush assembly 109. For example, the push button assembly 113 used with a dual flush assembly may include a first button for activation of a quick flush mode with a reduced amount of water usage and a second button for activation of a full flush mode using the standard amount of water.

Figure 2:
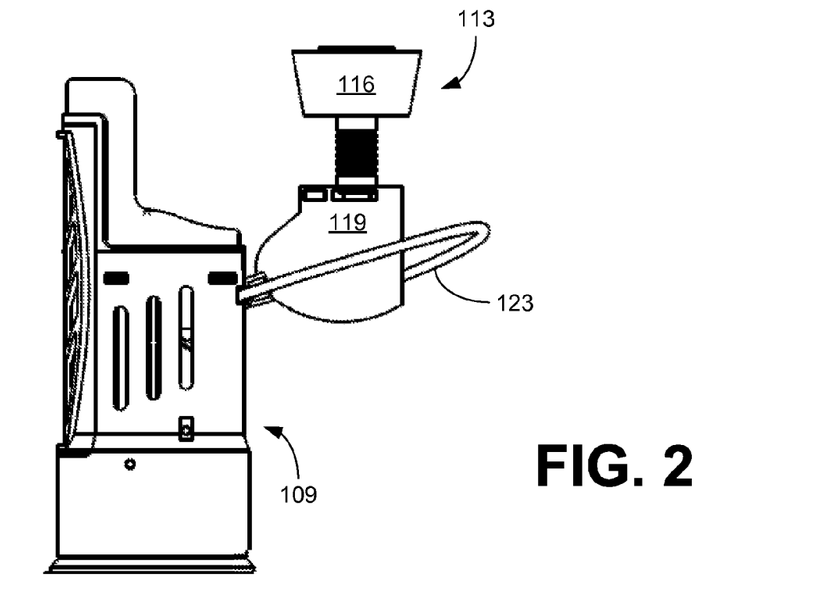
FIG. 2 is a drawing of a dual flush toilet system with push button activation of a dual flush assembly used in the toilet of FIG. 1 according to various embodiments of the disclosure.
Figure 3:
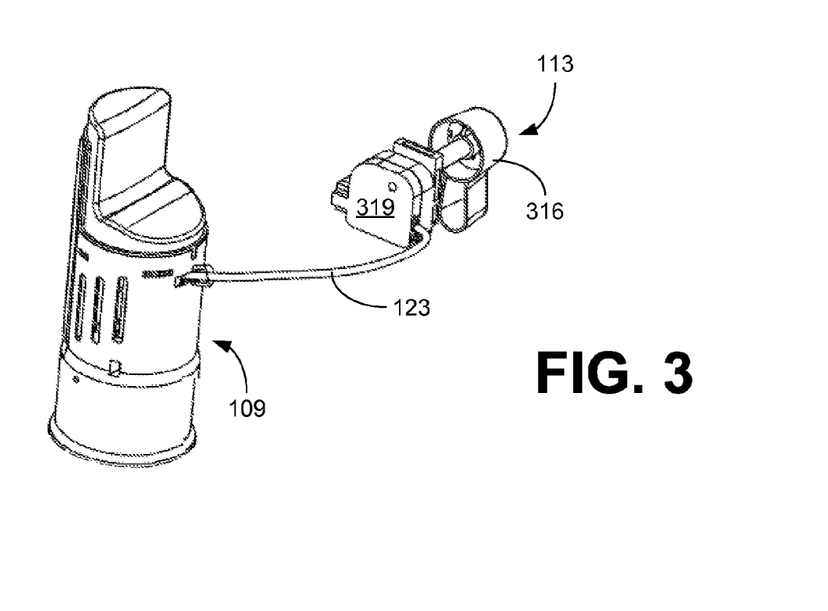
FIG. 3 is a drawing of a dual flush toilet system with rotary handle activation of a dual flush assembly used in the toilet of FIG. 1 according to various embodiments of the disclosure.

As illustrated in FIG. 2, the actuation control box 119 may be in communication with the flush assembly 109 through a cable assembly 123, which is connected to the actuation control box 119 and the flush assembly 109. In alternative embodiments, an activation assembly 113 includes a rotary handle assembly 316 that is detachably connected to an actuation control box 319 in communication with the flush assembly 109 as illustrated in FIG. 3. Rotation of the rotary handle assembly 316 to one or more predetermined position(s) initiates appropriate operation of the flush assembly 109. For example, for a dual flush assembly, rotation of the rotary handle assembly 316 from a neutral position to an intermediate position activates the quick flush mode and further rotation to a full rotation position initiates the full flush mode. Other flush assemblies 109 may utilize different activation assemblies 113 as appropriate.

Referring next to FIGS. 4A-4H, shown is an example of the air freshener assembly 103 of FIG. 1. In the embodiment of FIGS. 4A-4H, the air freshener assembly 103 includes a spray head 129, the position of which may be adjusted using a thumb wheel 133. The air freshener assembly 103 may also include a selector switch 136 that is configured to select the length of time for which an aerosol is dispensed by the air freshener assembly 103 based upon the position of the selector switch 136. The selector switch 136 may also be configured to disable operation of the air freshener assembly 103 when in a predefined position. In some embodiments, the selector switch 136 is configured to select between disabling operation of the air freshener assembly 103 or enabling operation with a fixed discharge time.

Figure 4A:
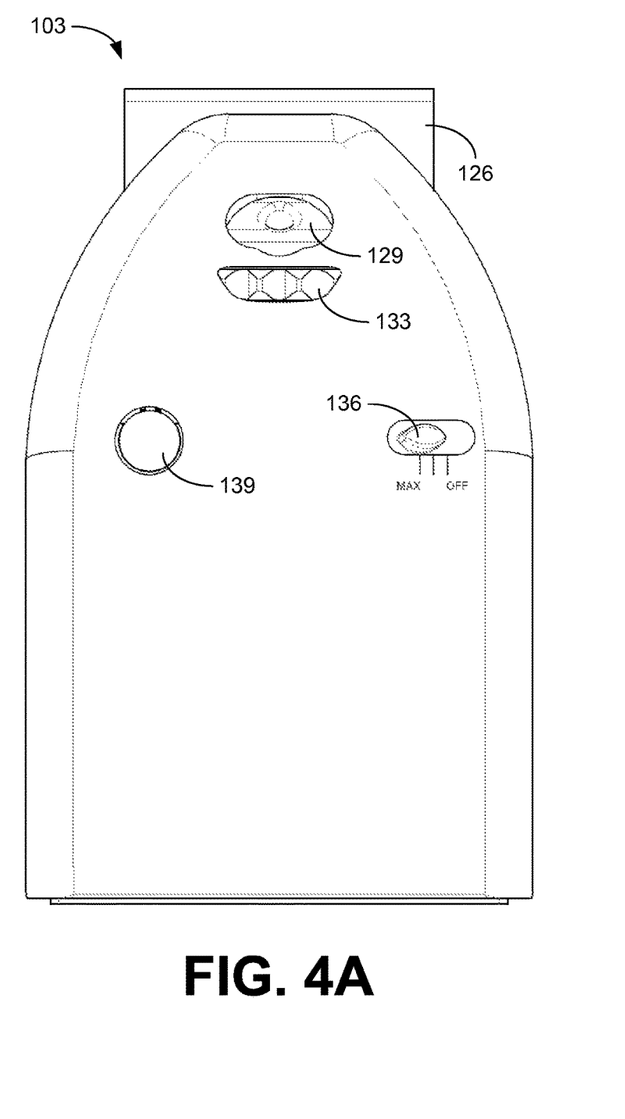
FIGS. 4A-4H are drawings that provide various views of an air freshener assembly of FIG. 1 according to various embodiments of the disclosure.
Figure 4B:
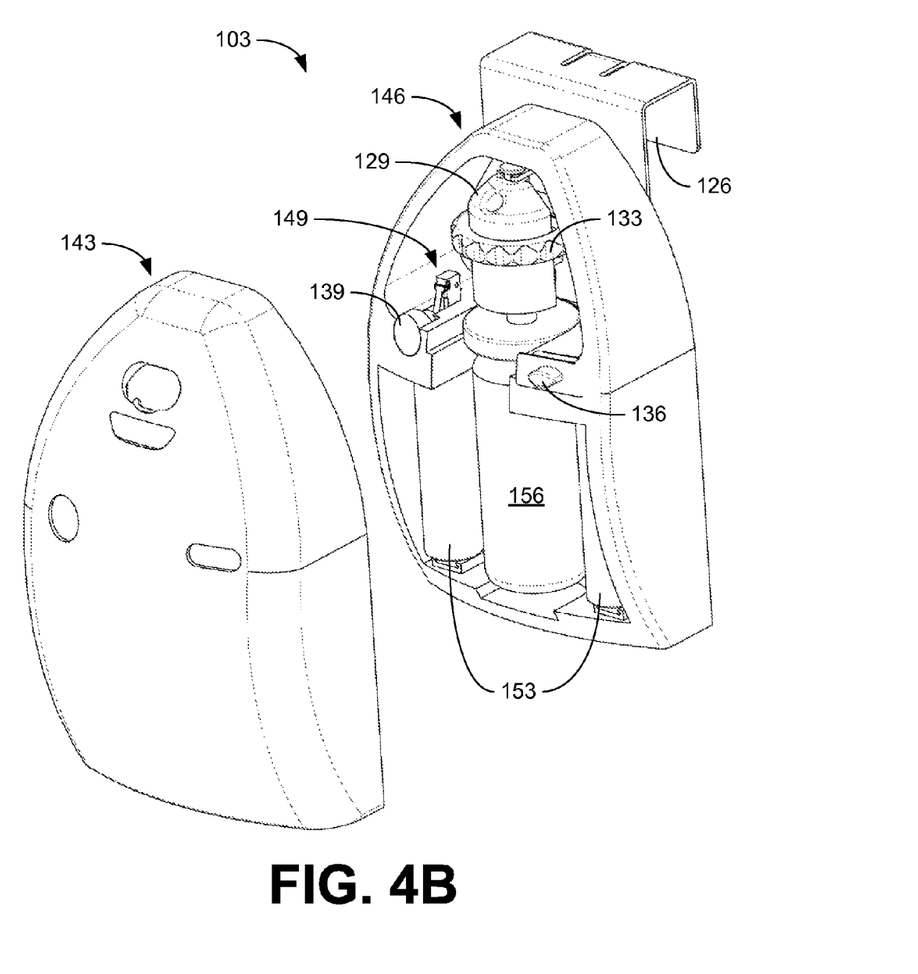

The air freshener assembly 103 also includes a manual initiation 139 to allow a user to initiate discharge of the aerosol. In the embodiment of FIG. 4A, the manual initiation 139 is a button that, when depressed, initiates the discharge cycle. Referring now to FIG. 4B, shown is a view of the air freshener assembly 103 with the assembly cover 143 removed from the assembly casing 146. Depressing the manual initiation 139 causes a switch 149 (e.g., a microswitch, a capacitive switch, or a magnetic switch) to close, initiating discharge of the aerosol. In some embodiments, a proximity sensor may be utilized. The air freshener assembly 103 also includes a power source (e.g., one or more batteries 153, a solar cell and/or other suitable low voltage power supply) to provide electric power to control circuitry housed within the assembly casing 146. In some embodiments, when the selector switch 136 is positioned to disable operation of the air freshener assembly 103, the manual initiation 139 may override the condition and initiate a discharge. In other embodiments, operation deactivation by the selector switch 139 also disables the manual initiation 139.

Figure 4C:
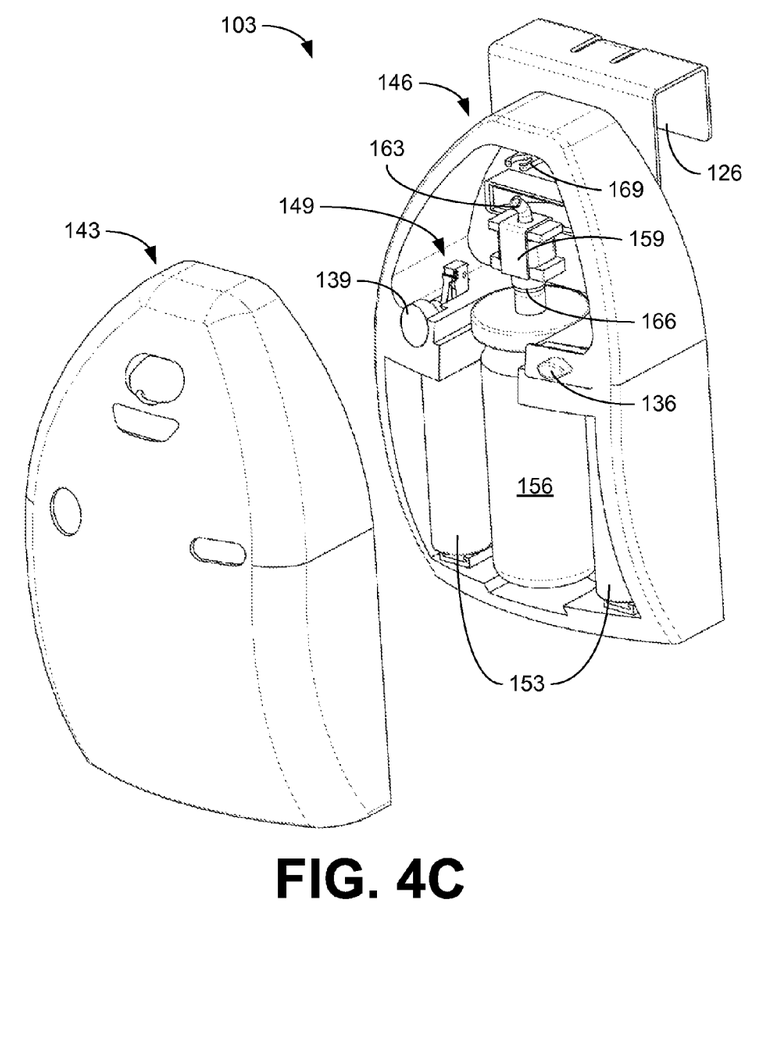

An aerosol cartridge 156 within the assembly casing 146 provides the aerosol spray for discharge. FIG. 4C shows the air freshener assembly 103 with the spray head 129 and thumb wheel 133 removed. The spray head 129 may be held in position by a lower support 166 and an upper clip 169. A control valve 159 (e.g., a solenoid valve) that is controlled by the control circuitry to release the aerosol spray through the spray head 129 via tube 163. Duration of discharge, as well as delay in starting discharge, may be controlled by the control circuitry. In some embodiments, the control circuitry may be configured to vary the discharge duration over time to account for a reduction in canister pressure over the lifetime of the aerosol canister 156.

Figure 4D:
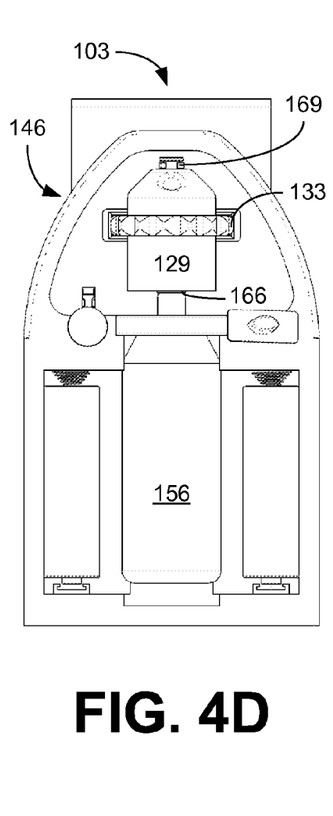
Figure 4E:
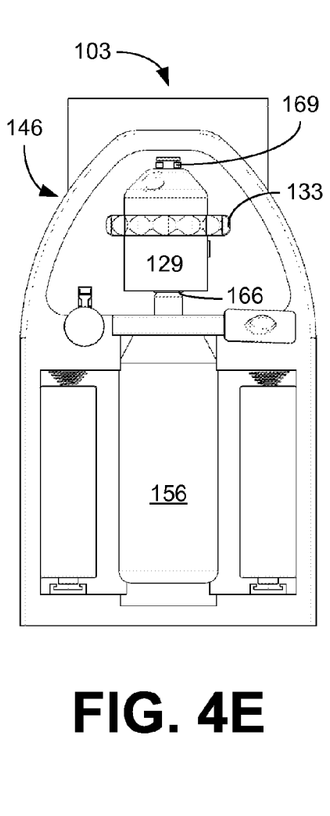
Figure 4F:
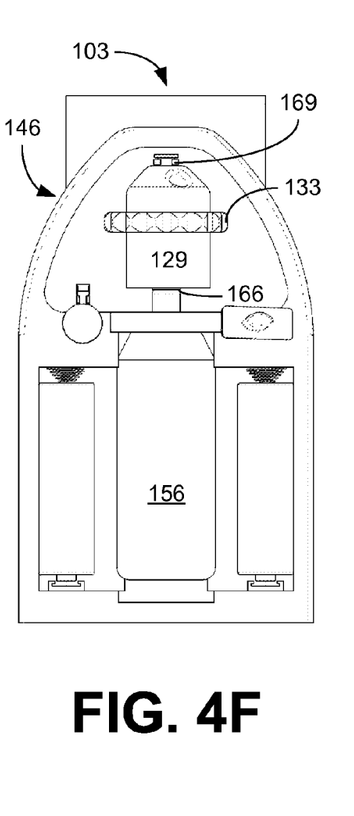

Referring next to FIGS. 4D-4F, the position of spray head 129 may be adjusted using a thumb wheel 133. FIG. 4D depicts that spray head 129 in a central position such as that illustrated in FIG. 4A. By using the thumb wheel 133, the spray head 129 may be turned to the left as in FIG. 4E or to the right as in FIG. 4F to direct the spray discharge as desired. In the embodiment of FIGS. 4D-4F, the spray head 129 rotates about the lower support 166 and the upper clip 169.

Figure 4G:
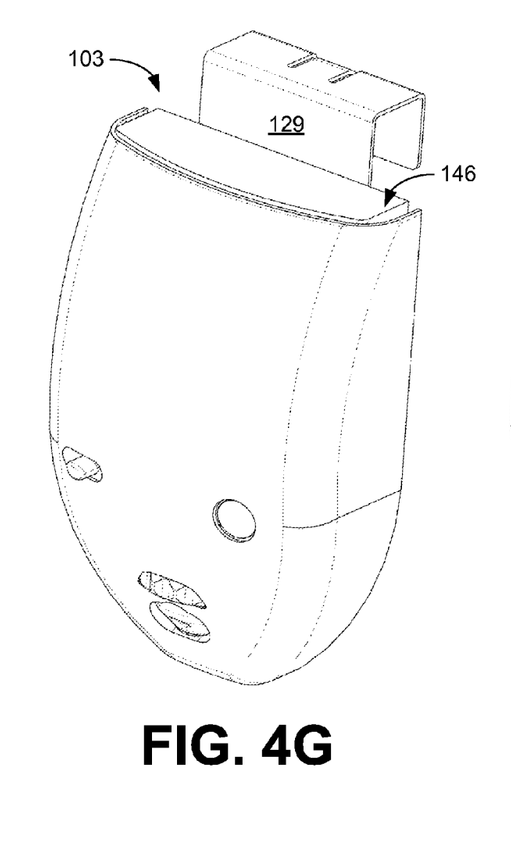
Figure 4H:
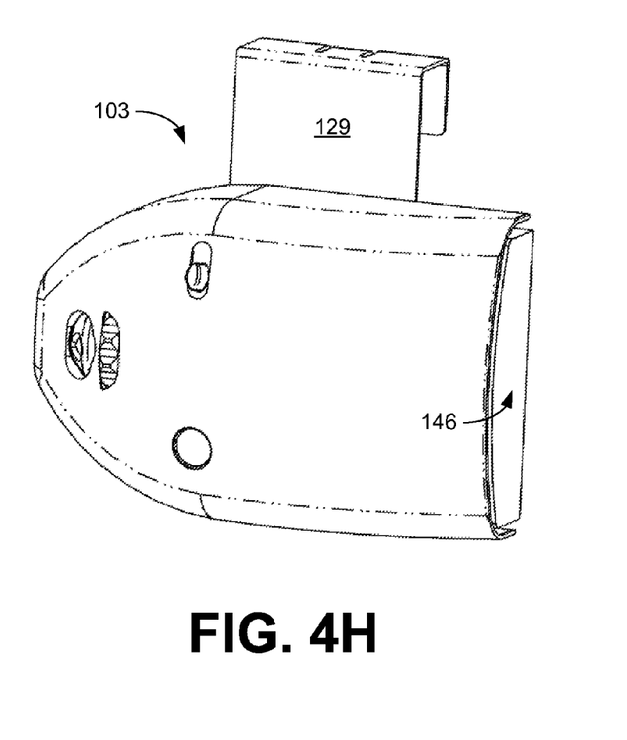

The orientation of the air freshener assembly 103 may also be adjusted to direct the spray discharge as illustrated in FIGS. 4G-4H. The mounting clip 126 is attached to the back of the assembly casing 146 and may be configured to allow the air freshener assembly 103 to be rotated about the attachment point. In some embodiments, the air freshener assembly 103 may be rotated in 90 degree increments as shown in FIGS. 4G and 4H. For example, the orientation of FIG. 4G directs the spray downward and away from a user of the toilet. In other embodiments, rotation of the air freshener assembly 103 may be in smaller increments. In some cases, the mounting clip 126 may be detached and reattached to the assembly casing 146 to provide the desired orientation.

Figure 5A:
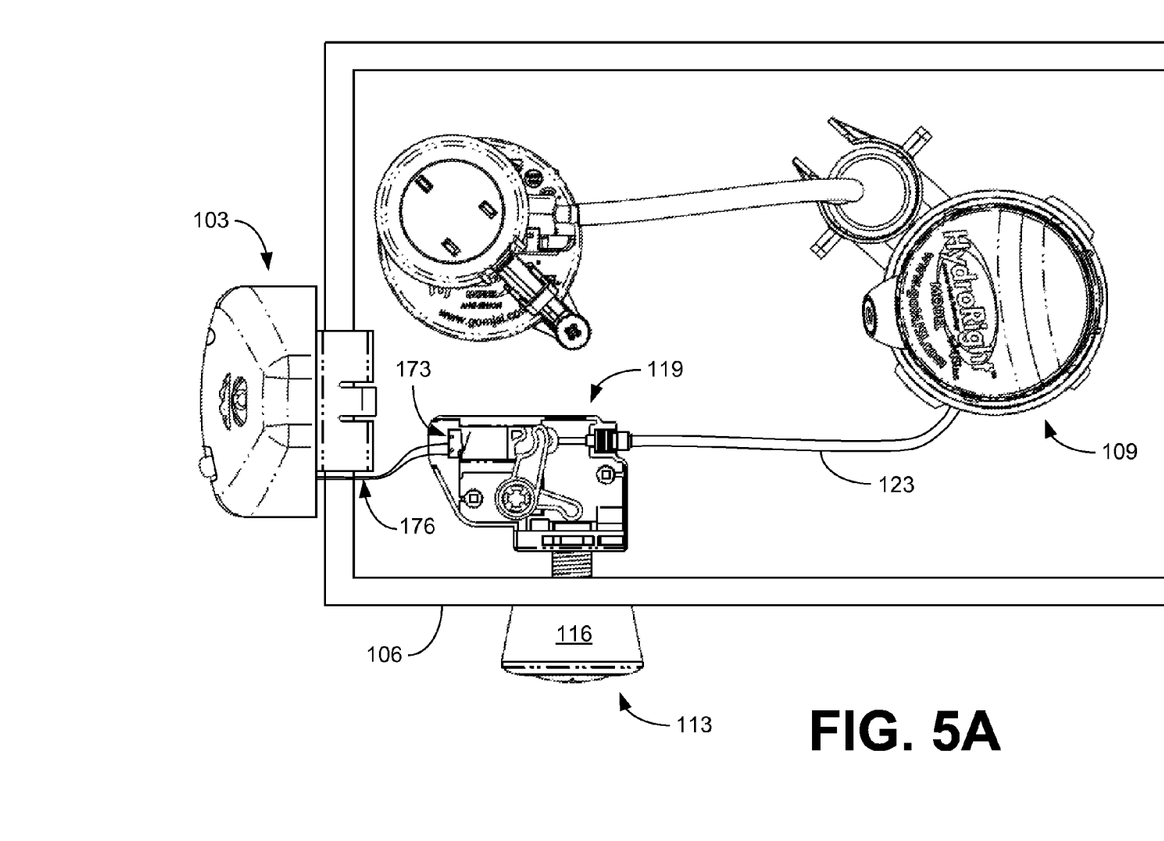
FIGS. 5A-5C are drawings that provide top views of an embodiment of the air freshener assembly of FIG. 1 according to various embodiments of the disclosure.
Figure 5B:
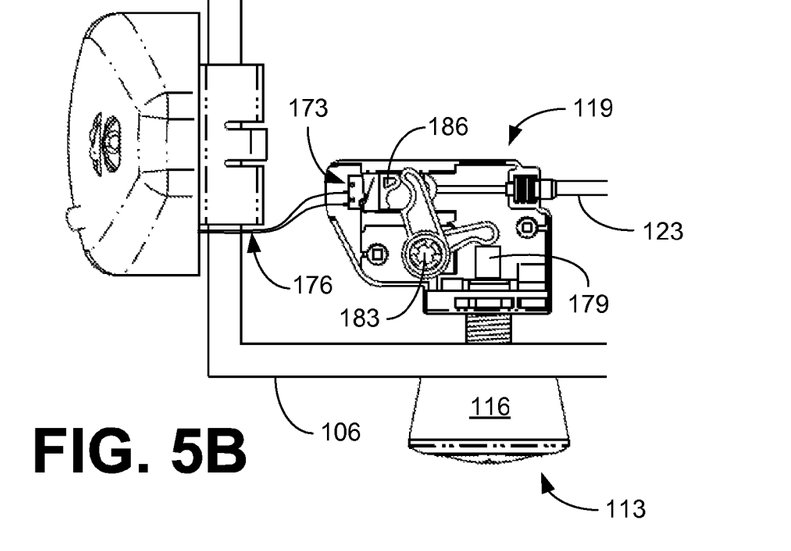
Figure 5C:
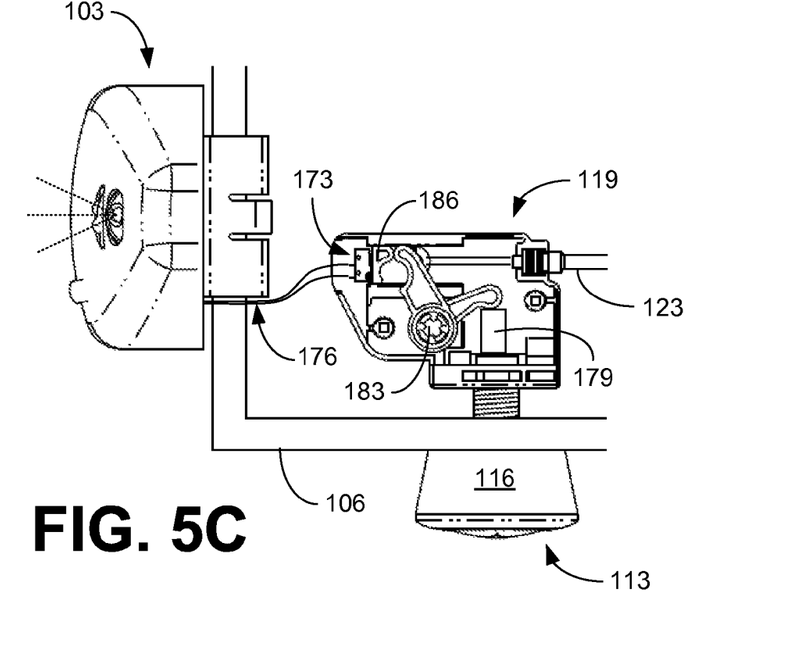

Referring now to FIG. 5A-5C, shown are top views of the air freshener assembly 103 affixed to the tank 106 of toilet 100 of FIG. 1. A cut away view of the actuation control box 119 is provided for clarity. In the embodiment of FIGS. 5A-5C, the actuation control box 119 includes a switch 173 (e.g., a micro-switch, capacitive switch, or magnetic switch). The switch 173 may be sealed to prevent moisture from entering the switch 173. The switch 173 is in communication with the air freshener assembly 103 through wire(s) 176 or other appropriate means.

Beginning with FIG. 5A, the activation assembly 113 is in a neutral position without a button of the push button assembly 116 depressed. With the activation assembly 113 in the neutral position, switch 173 is open and the air freshener assembly 103 remains at rest. Referring next to FIG. 5B, depressing a button of the push button assembly 116 extends a plunger 179 from the end of the push button assembly 116 into the actuation control box 113. Extension of plunger 179 causes a cam 183 to rotate about a fixed point, engaging with a cable anchor 186 that detachably connects one end of a cable of cable assembly 123. The cable anchor 186 moves within a guide track to retract the cable into the actuation control box 119. As the plunger 179 reaches an intermediate position, as illustrated in FIG. 5B, the switch 173 is open and the air freshener assembly 103 remains at rest. Further extension of plunger 179, as illustrated in FIG. 5B, causes the cable anchor 186 to move to the end of the guide track, closing switch 173 and activating the air freshener assembly 103.

In the case where the activation assembly 113 initiates operation of a dual flush assembly, extension of the plunger 179 to the intermediate position of FIG. 5B activates the quick flush mode and extension of the plunger 179 to the full extension position of FIG. 5C initiates the full flush mode. In some embodiments, a single button is used to extend the plunger 179. In other embodiments, separate buttons for intermediate extension to activate the quick flush mode and full extension to activate the full flush mode are included in the push button assembly 116. Similarly, rotation of the cam 183 can be provided by the rotary handle assembly 316 of FIG. 3. Rotation of the rotary handle assembly 316 from a neutral position to an intermediate position activates the quick flush mode without closing switch 173. Further rotation to a full rotation position initiates the full flush mode and closes switch 173, thereby activating the air freshener assembly 103.

Figure 6:
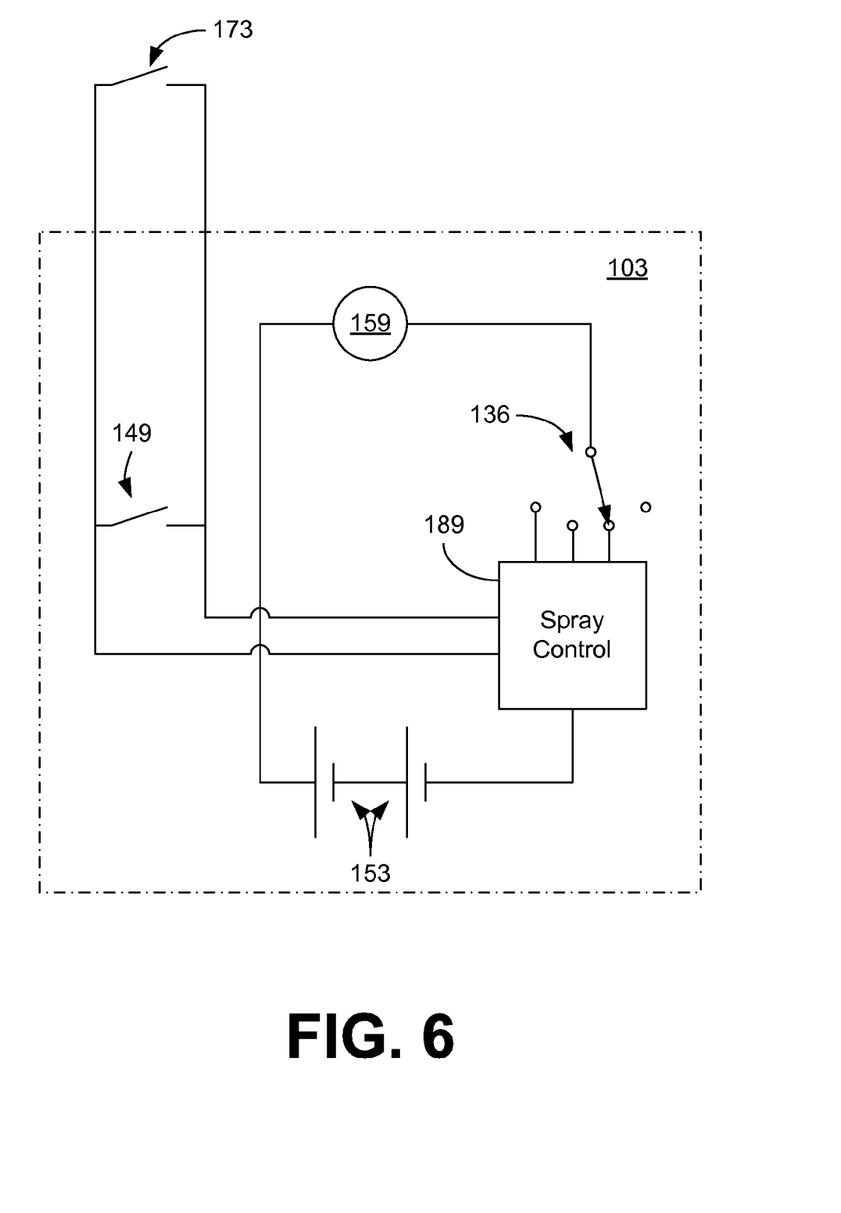
FIG. 6 is a block diagram of control circuitry of the air freshener assembly of FIG. 1 according to various embodiments of the disclosure.

Operation of the air freshener assembly 103 will now be discussed with reference to FIG. 6, which is a block diagram of the control circuitry of the air freshener assembly 103. When the switch 173 (FIGS. 5A-5C) is closed, a spray control 189 is activated, causing the control valve 159 to initiate (e.g., by energizing a coil of the control valve 159 through batteries 153) discharge of aerosol from the aerosol cartridge 156. In some embodiments, aerosol discharges as long as the switch 173 is closed. In other embodiments, closing the switch 173 initiates discharge for a predefined time. In the embodiment of FIG. 6, closing the switch 149 with the manual initiation 139 (FIGS. 4A-4C) will bypass switch 173 to initiate discharge of the aerosol. In other embodiments, the manual initiation 139 and the switch may have separate inputs to the spray control 189.

In the embodiments of FIGS. 4A-4C and 6, the positioning of the selector switch 136 selects the length of time for which an aerosol is dispensed by the air freshener assembly 103. For example, the position of the selector switch 136 may select circuitry within the spray control 189 to vary the discharge time from a maximum time to a minimum time. The selector switch 136 may include one or more intermediate positions corresponding to discharge times between the maximum and minimum times. The selector switch may also include an off position to disable operation of the air freshener assembly 103. In the embodiment of FIG. 6, the connection to the control valve 159 is disconnected when in the off position.

In other embodiments, the off position may select circuitry for a discharge time of zero seconds. While the selector switch 136 is depicted in FIG. 6 as connected in series with the control valve 159 and batteries 153, in other embodiments the selector switch 136 may be an input to the spray control 189 similar to switches 173 and 149.

The spray control 189 may also include a spray lock-out timer configured to provide a predefined time delay before a subsequent aerosol discharge can be initiated. The spray lock-out timer may be configured to allow discharges to be initiated only after the predefined time delay has elapsed. For example, the next discharge is prevented unless an interval of one minute or more has passed from the last discharge initiation. In some embodiments, the time delay is fixed. In other embodiments, the time delay may be adjusted by the spray control 189 based upon the discharge time selected by selector switch 136 or it may be configured by a user of the air freshener assembly 103.

In addition, the spray control 189 may also include a timer configured to automatically initiate an aerosol discharge after a predefined time period has exceeded. For example, if one hour has passed from the previous initiation of a discharge, then the spray control 189 automatically initiates another discharge. The predefined time period may be configured by the user of the air freshener assembly 103 or adjusted by the spray control 189 based upon the discharge time selected by selector switch 136.

Figure 7:
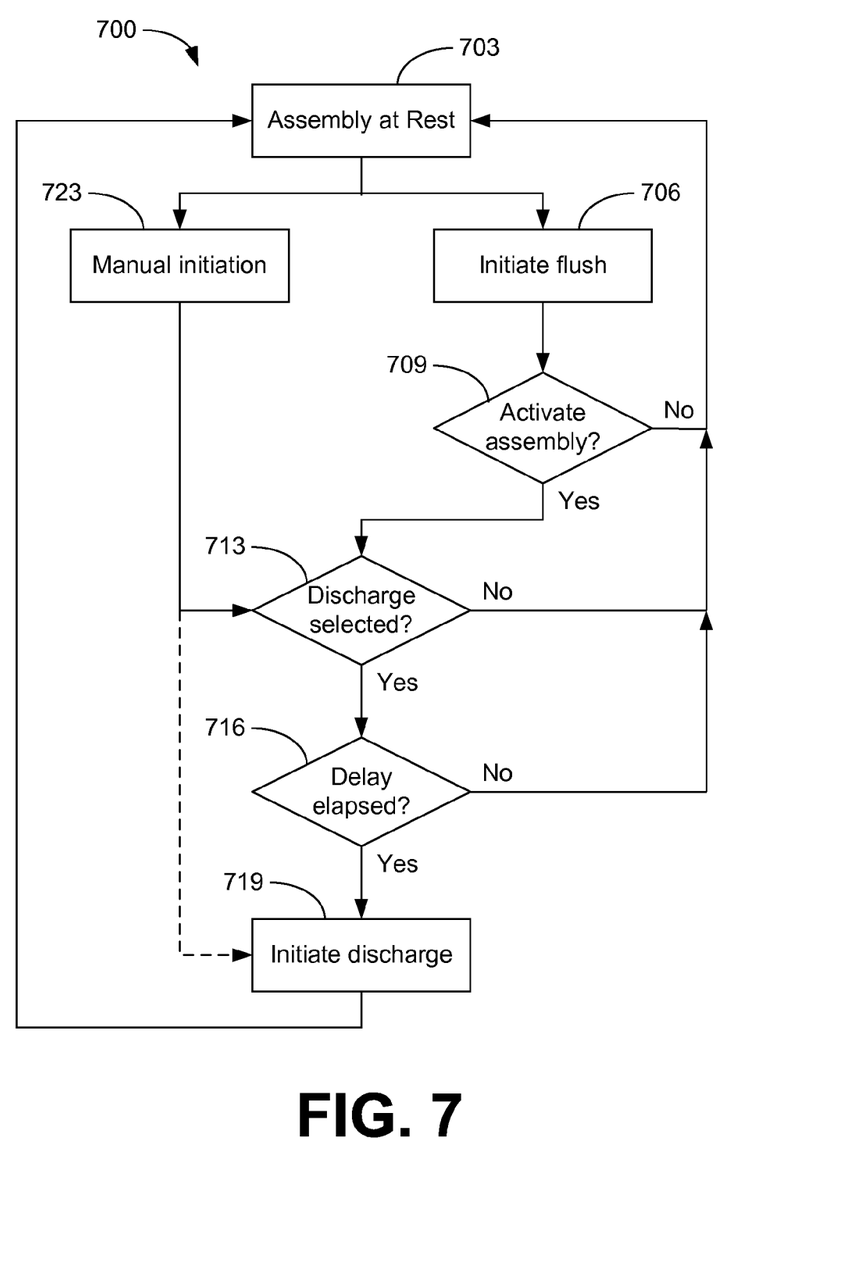
FIG. 7 is a flowchart illustrating functionality and operation of the air freshener assembly of FIG. 1 according to various embodiments of the present disclosure.

Referring now to FIG. 7, shown is a flowchart 700 illustrating functionality and operation of the air freshener assembly 103 of FIG. 1. To begin, the air freshener assembly 103 is at rest in block 703. A flush of the toilet 100 (FIG. 1) may be initiated in block 706 through an activation assembly 113. For example, a button of a push button assembly 116 (FIG. 2) may be depressed or a rotary handle may be rotated of a rotary handle assembly 316 (FIG. 3). Upon sufficient depression or rotation of the activation assembly 113, the air freshener assembly 103 is activated in block 709.

As illustrated in FIGS. 5A-5C, depressing the button of the push button assembly 116 to fully extend the plunger 179 closes switch 173 as depicted in FIG. 5C, thereby activating the air freshener assembly 103. Depression of the button to an intermediate position as illustrated in FIG. 5B, does not close switch 173 and the air freshener assembly 103 remains at rest in block 703. Similarly, full rotation of a rotary handle assembly 316 from a neutral position closes switch 173 to activate the air freshener assembly 103, while intermediate rotation of the rotary handle assembly 316 does not close switch 173 and the air freshener assembly 103 remains at rest in block 703.

Operation of the air freshener assembly 103 is determined in block 713. If the selector switch 136 is positioned to disable operation of the air freshener assembly 103, then the air freshener assembly 103 remains at rest in block 703. Otherwise, the position of the selector switch 136 is used to determine the discharge time of the aerosol spray. The position of the selector switch 136 determines the length of time the aerosol is discharged. A predefined length of time corresponds to each selector switch position.

In block 716, it may be determined if sufficient time has elapsed since the previous aerosol discharge. For example, if a predefined time delay has not been met, then the air freshener assembly 103 remains at rest in block 703. In some embodiments, the time delay is fixed. In other embodiments, the time delay may be adjusted based upon the discharge time selected by selector switch 136. If the time delay has elapsed, then discharge of the aerosol is initiated in block 719. After the aerosol is dispensed, the air freshener assembly 103 returns to rest in block 703.

Manual initiation of a discharge may also be initiated from rest in block 723. Depressing the manual initiation 139 (FIG. 4A) activates the air freshener assembly 103 to initiate a discharge of aerosol. Operation of the air freshener assembly 103 may be determined in block 713 based upon the position of the selector switch 136. In some embodiments, if the selector switch 136 is positioned to disable operation of the air freshener assembly 103, then the manual initiation 139 is also disabled and the air freshener assembly 103 remains at rest in block 703. In other embodiments, the manual initiation 139 overrides the condition and proceeds to block 716, where it may be determined if sufficient time has elapsed since the previous aerosol discharge. If so, then a discharge is initiated in block 719. If not, then the air freshener assembly 103 remains at rest in block 703.

In some embodiments, the manual initiation 139 may bypass the disablement of block 713 and the time delay of block 716 to initiate a discharge of aerosol in block 719. The discharge may be for a fixed time period or may be based upon the discharge time selected by selector switch 136. After the aerosol is dispensed, the air freshener assembly 103 returns to rest in block 703.

Although the flowchart 700 of FIG. 7 shows a specific order of execution, it is understood that the order of execution may differ from that which is depicted. For example, the order of execution of two or more blocks may be scrambled relative to the order shown. Also, two or more blocks shown in succession in FIG. 7 may be executed concurrently or with partial concurrence. Further, in some embodiments, one or more of the blocks shown in FIG. 7 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Figure 8A:
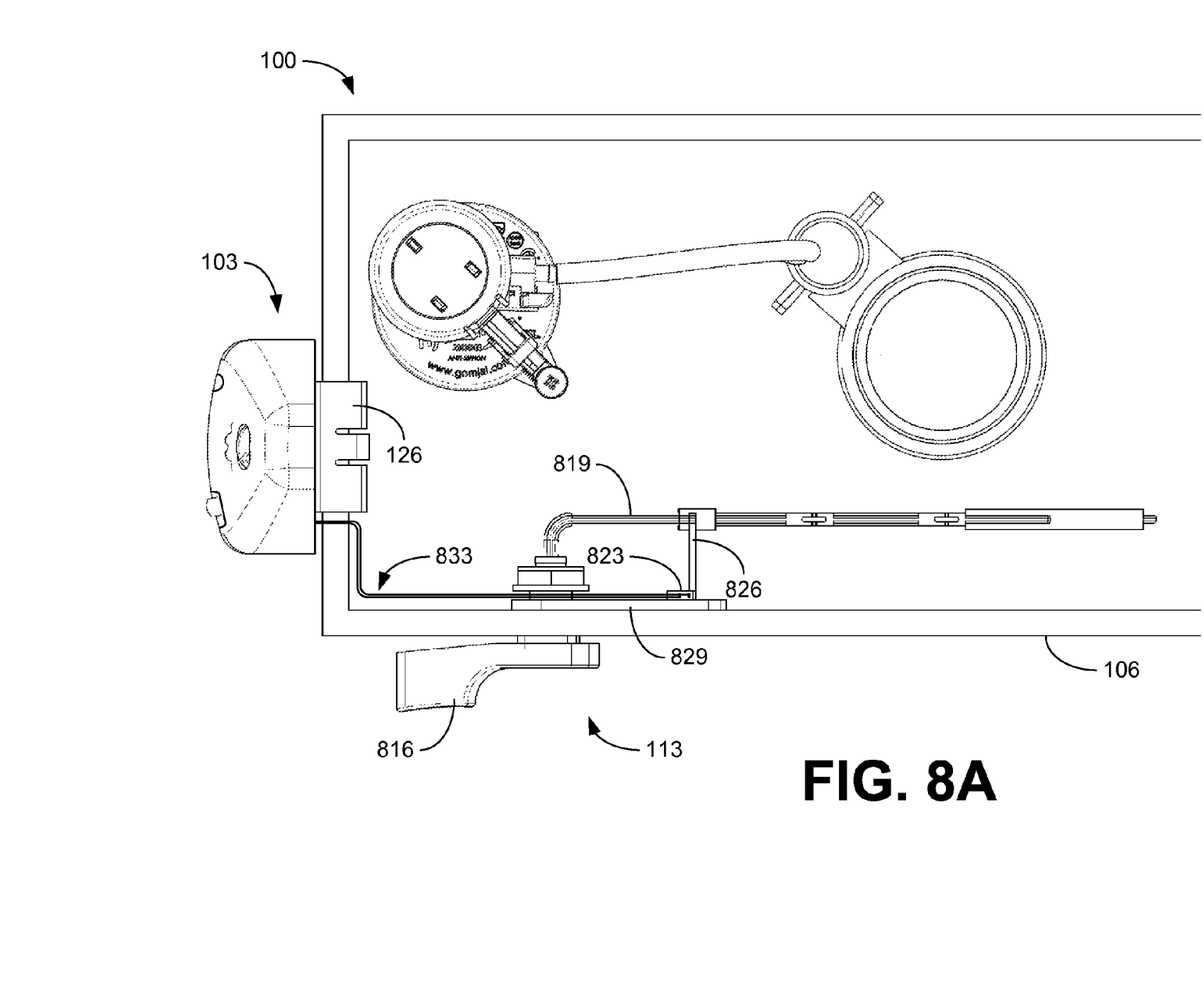
FIGS. 8A-8B and 9 are drawings that provide various views illustrating various ways to activate the air freshener assembly of FIG. 1 according to various embodiments of the disclosure.
Figure 8B:
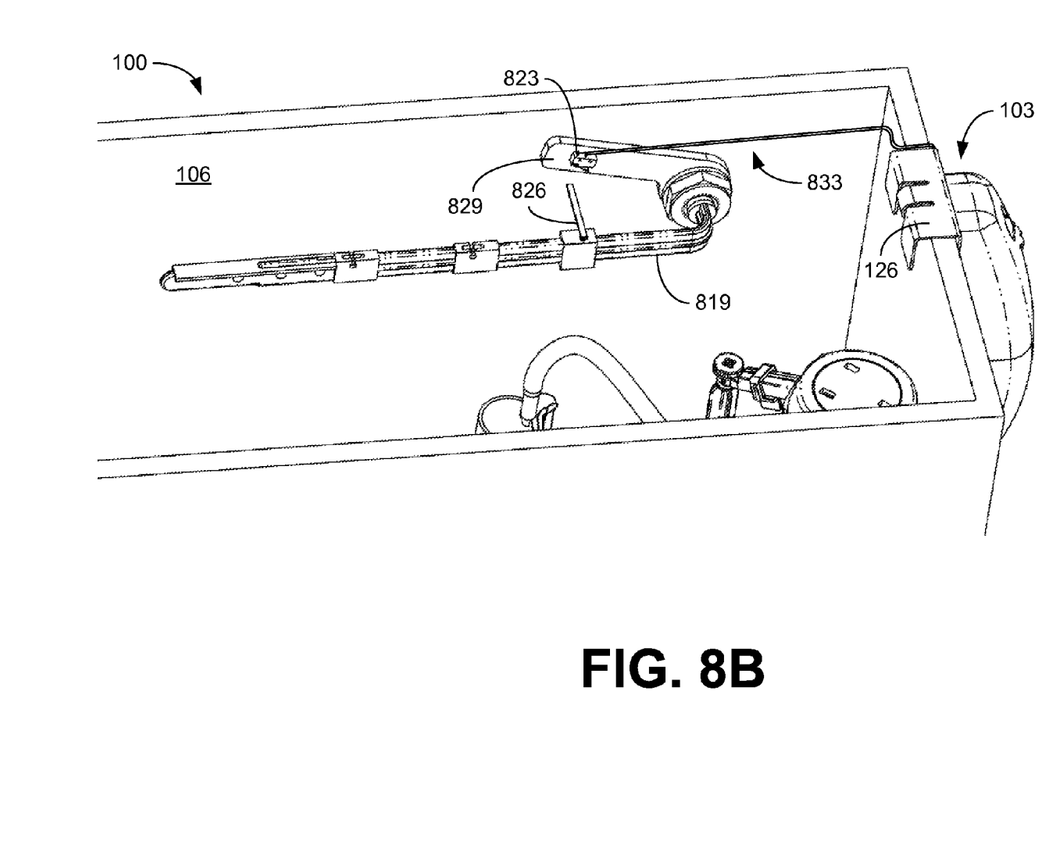

Referring next to FIGS. 8A-8B, shown are various views illustrating other means for activation of the air freshener assembly 103 of FIG. 1. In FIGS. 8A-8B, the activation assembly 113 includes a flush handle 816 secured to a lever arm 819 that is used to lift a flapper valve to initiate a flush of the toilet 100. The lever arm 819 is configured to close a switch 823 when the lever arm 819 is sufficiently rotated by the flush handle 816. In the embodiment of FIGS. 8A-8B, a switch extension 823 is connected to the lever arm 819 to extend towards the wall of the toilet tank 106. The switch extension 823 may be detachably connected to the lever arm 819. The position of the switch extension 823 may also be adjustable along the length of the lever arm 819.

The switch 823 may be a micro-switch, capacitive switch, or magnetic switch that is closed by proximity and/or contact of the switch extension 823. In some embodiments, the switch 823 is mounted in position on the wall of the tank 106. In the embodiment of FIGS. 8A-8B, a mounting plate 829 is used to secure the switch 823 in position by the activation assembly 113. The switch 823 may be sealed to prevent moisture from entering the switch 823. The switch 823 is in communication with the air freshener assembly 103 through wire(s) 833 or other appropriate means. Closing of the switch 823 activates the air freshener assembly 103 as described previously.

In other embodiments, a switch to activate the air freshener assembly may be integrated into the activation assembly 113 of FIGS. 8A-8B at different locations. For example, a rotary switch may be included where the flush handle 816 connects with the lever arm 819. Rotation of the flush handle 816 and lever arm 819 would close the rotary switch, activating the air freshener assembly 103 as described. Other switches may be used such as, but not limited to, a mercury switch, a reed switch, a tilt style switch, etc.

Figure 9:
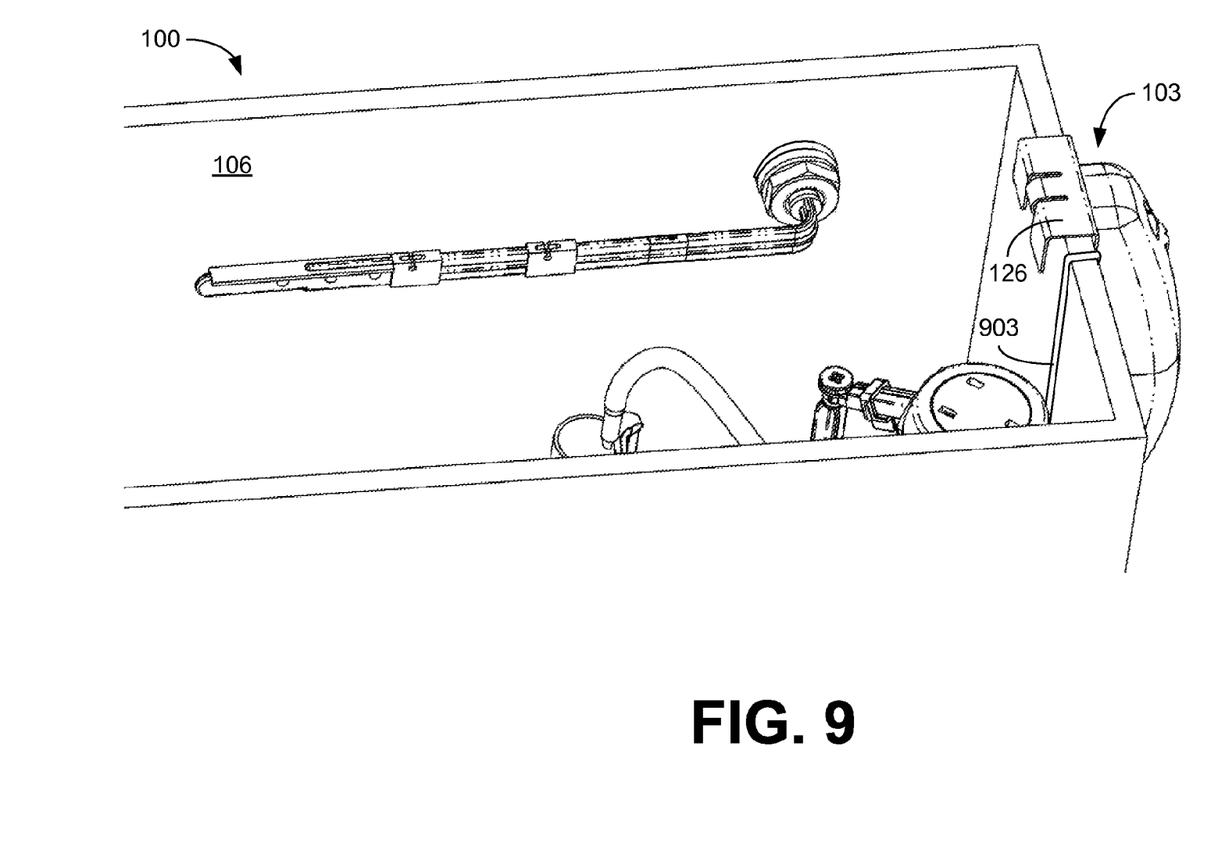

FIG. 9 illustrates another means for activation of the air freshener assembly 103 of FIG. 1. In the embodiment of FIG. 9, a sensing tube 903 in communication with a pressure detector of the air freshener assembly 103 extends below the water level in the toilet tank 106. When a flush is initiated, the water level in the tank 106 drops as the water drains from the tank 106, causing a pressure drop in the sensing tube 903. The pressure detector senses the decrease in pressure. The pressure detector is configured to activate the air freshener assembly 103 (e.g., close a switch or a transistor) based upon the pressure drop and initiate a discharge of aerosol as previously described. Refilling the tank 106 with water after the flush increases the pressure in the sensing tube 903, which is sensed by the pressure detector.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. An air freshener assembly for a toilet system, comprising:
   a control valve coupled to an aerosol cartridge; and
   a spray control in communication with a switch of a flush activation assembly, where the switch is configured to close in response to initiation of a full flush of the toilet system and to remain open in response to a quick flush of the toilet system, and where the spray control is configured to activate the control valve to discharge aerosol from the aerosol cartridge in response to the switch being closed.

2. The air freshener assembly of claim 1, wherein the flush activation assembly of the toilet system is configured to transition from a neutral position to an intermediate position to initiate the quick flush, and further transition to a full position to initiate a full flush.

3. The air freshener assembly of claim 1, further comprising a selector switch configured to select one of a plurality of predefined discrete lengths of time for which the aerosol is dispensed by the air freshener assembly.

4. The air freshener assembly of claim 3, wherein the selector switch is further configured to disable operation of the air freshener assembly.

5. The air freshener assembly of claim 1, further comprising a manual initiation configured to activate the control valve to discharge aerosol without initiation of a flush of the toilet system.

6. The air freshener assembly of claim 1, wherein the spray control is further configured to discharge the aerosol for a predefined length of time corresponding to a position of a selector switch.

7. The air freshener assembly of claim 1, wherein the spray control is further configured to prevent discharge of the aerosol if a predefined time delay from a previous discharge of aerosol has not elapsed.

8. The air freshener assembly of claim 7, wherein a manual initiation bypasses the predefined time delay to initiate discharge of the aerosol without initiation of a flush of the toilet system.

9. The air freshener assembly of claim 1, wherein the air freshener assembly is mounted on a tank of the toilet system.

10. A method, comprising:
    sensing an initiation of a flush of a toilet system; and
    discharging aerosol from a canister for a predefined discharge time in response to sensing the initiation of the flush, the predefined discharge time selected from a plurality of discrete predefined discharge times.

11. The method of claim 10, wherein the predefined discharge time varies over time based upon aerosol usage over a lifetime of the canister.

12. The method of claim 10, wherein the predefined discharge time is selected from a plurality of predefined discharge times using a selector switch.

13. The method of claim 10, wherein the aerosol is not discharged if a predefined time delay from the previous discharge of aerosol has not elapsed.

14. The method of claim 10, wherein the toilet system is a dual flush toilet system configured to discharge a first predetermined amount of water for a quick flush and a second predetermined amount of water for a full flush, the second predetermined amount of water greater than the first predetermined amount of water.

15. A toilet system, comprising:
    means for initiating a flush of a toilet;
    means for sensing initiation of the flush; and
    means for discharging aerosol in response to sensing the initiation of the flush, where the aerosol is discharged for a predefined discharge time that is selected from a plurality of discrete predefined discharge times.

16. The toilet system of claim 15, wherein the means for discharging aerosol further comprises means for selecting the predefined discharge time from the plurality of discrete predefined discharge times.

17. The toilet system of claim 15, wherein the means for discharging aerosol further comprises means for manually initiating an aerosol discharge.

18. The toilet system of claim 15, wherein the toilet is a dual flush toilet configured to discharge a first fixed amount of water for a quick flush and a second fixed amount of water for a full flush, the second fixed amount of water greater than the first fixed amount of water.

19. The toilet system of claim 18, wherein the means for sensing initiation of the flush distinguishes between activation of a full flush and activation of a quick flush.

20. The toilet system of claim 15, wherein the means for sensing initiation of the flush comprises a pressure detector.

21. The toilet system of claim 20, wherein the pressure detector is configured to sense a pressure drop caused by water draining from a tank of the toilet system.

22. The toilet system of claim 16, wherein the means for selecting the predefined discharge time is further configured to disable operation of the means for discharging aerosol.

* * * * *